(12) United States Patent
Chen et al.

(10) Patent No.: US 12,005,427 B2
(45) Date of Patent: Jun. 11, 2024

(54) CATALYST FOR METHANATION REACTION AND METHOD FOR PREPARING METHANE

(71) Applicant: INDUSTRIAL TECHNOLOGY RESEARCH INSTITUTE, Hsinchu (TW)

(72) Inventors: Yen-Chih Chen, Changhua (TW); Man-Yin Lo, Zhubei (TW); Hsi-Yen Hsu, Hsinchu (TW); Ying-Chieh Lee, Hsinchu (TW); Yuan-Peng Du, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 17/946,747

(22) Filed: Sep. 16, 2022

(65) Prior Publication Data

US 2023/0146325 A1 May 11, 2023

Related U.S. Application Data

(60) Provisional application No. 63/277,836, filed on Nov. 10, 2021.

(30) Foreign Application Priority Data

Jul. 19, 2022 (TW) ................................ 111126958

(51) Int. Cl.
| | | |
|---|---|---|
| *B01J 23/755* | (2006.01) | |
| *B01J 21/06* | (2006.01) | |
| *B01J 23/10* | (2006.01) | |
| *B01J 35/00* | (2024.01) | |
| *B01J 35/08* | (2006.01) | |
| *B01J 35/23* | (2024.01) | |
| *B01J 35/30* | (2024.01) | |
| *B01J 35/51* | (2024.01) | |
| *C07C 1/04* | (2006.01) | |

(52) U.S. Cl.
CPC ........... *B01J 23/755* (2013.01); *B01J 21/066* (2013.01); *B01J 23/10* (2013.01); *B01J 35/23* (2024.01); *B01J 35/393* (2024.01); *B01J 35/51* (2024.01); *C07C 1/043* (2013.01); *C07C 2521/06* (2013.01); *C07C 2523/10* (2013.01); *C07C 2523/755* (2013.01)

(58) Field of Classification Search
CPC ........ B01J 23/755; B01J 23/10; B01J 21/066; B01J 35/0013; B01J 35/006; B01J 35/08; C07C 1/043
See application file for complete search history.

(56) References Cited

U.S. PATENT DOCUMENTS

| | | | |
|---|---|---|---|
| 8,148,295 B2 | 4/2012 | Augustine | |
| 9,539,543 B2 | 1/2017 | Gramiccioni | |
| 9,548,498 B2 | 1/2017 | Klose-Schubert et al. | |
| 9,802,872 B2 | 10/2017 | Chen et al. | |
| 10,478,808 B2 * | 11/2019 | D'Souza | ................ B01J 23/18 |
| 2019/0160427 A1 | 5/2019 | Deeba et al. | |
| 2019/0168205 A1 | 6/2019 | Sasmaz et al. | |

FOREIGN PATENT DOCUMENTS

| | | |
|---|---|---|
| CN | 101920208 B | 9/2012 |
| CN | 103706373 A | 4/2014 |
| CN | 104148065 A | 11/2014 |
| CN | 104475119 A | 4/2015 |
| CN | 107890870 A | 4/2018 |
| CN | 113145123 A | 7/2021 |
| TW | 443944 B | 7/2001 |
| TW | 201808447 A | 3/2018 |
| WO | WO 2008/101875 A1 | 8/2008 |
| WO | WO 2010/006386 A2 | 1/2010 |

OTHER PUBLICATIONS

Zhao et al., Catalysis Communications, (2017), v101, p. 138-141.*
Taiwanese Office Action and Search No. 111126958, dated Jul. 14, 2023.
Botzolaki et al., "$CO_2$ Methanation on Supported Rh Nanoparticles: The Combined Effect of Support Oxygen Storage Capacity and Rh Particle Size", Catalysts 2020, vol. 10, No. 8, 944, pp. 1-25.
Garbarino et al., "A Study of Ni/La-$Al_2O_3$ Catalysts: A Competitive System for $CO_2$ Methanation", Elsevier, Applied Catalysis B: Environmental, 2019, vol. 248, pp. 286-297.
Li et al., "Cerium-Modified Ni-$La_2O_3$/$ZrO_2$ for $CO_2$ Methanation", Elsevier, Journal of Energy Chemistry, 2020, vol. 43, pp. 155-164.
Lin et al., "Crystal Phase Effects on the Structure and Performance of Ruthenium Nanoparticles for $CO_2$ Hydrogenation", Catalysis Science & Technology, 2014, vol. 4, No. 7, pp. 2058-2063.
Riani et al., "Ni/$SiO_2$—$Al_2O_3$ Catalysts for $CO_2$ Methanation: Effect of $La_2O_3$ Addition", Elsevier, Applied Catalysis B: Environmental, 2021, vol. 284, 119697, pp. 1-12.
Sakpal et al., "Structure-Dependent Activity of $CeO_2$ Supported Ru Catalysts for $CO_2$ Methanation", Elsevier, Journal of Catalysis, 2018, vol. 367, pp. 171-180.
Tada et al., "Ni/$CeO_2$ Catalysts with High $CO_2$ Methanation Activity and High $CH_4$ Selectivity at Low Temperatures", Elsevier, International Journal of Hydrogen Energy, 2012, vol. 37, No. 7, pp. 5527-5531.

(Continued)

*Primary Examiner* — Yong L Chu
(74) *Attorney, Agent, or Firm* — Birch, Stewart, Kolasch & Birch, LLP (57) ABSTRACT

A catalyst for methanation reaction and a method for preparing methane are provided. The catalyst for methanation reaction includes a core, a shell encapsulating the core, and an active metal. The core includes cerium dioxide ($CeO_2$), the shell includes zirconium dioxide ($ZrO_2$), and the active metal is in particle form and is disposed on an outer surface of the shell layer.

20 Claims, 3 Drawing Sheets

(56) References Cited

OTHER PUBLICATIONS

Tan et al., "Highly Dispersed and Stable Ni Nanoparticles Confined by MgO on $ZrO_2$ for $CO_2$ Methanation", Elsevier, Applied Surface Science, 2019, vol. 481, pp. 1538-1548.

Vrijburg et al., "Ceria-Zirconia Encapsulated Ni Nanoparticles for $CO_2$ Methanation", Catalysis Science & Technology, 2019, vol. 9, No. 18, pp. 5001-5010.

Xu et al., "Facile $Cr^{3+}$-Doping Strategy Dramatically Promoting $Ru/CeO_2$ for Low-Temperature $CO_2$ Methanation: Unraveling the Roles of Surface Oxygen Vacancies and Hydroxyl Groups", ACS Catalysis, 2021, vol. 11, No. 9, pp. 5762-5775.

Ye et al., "High-Performance of Nanostructured $Ni/CeO_2$ Catalyst on $CO_2$ Methanation", Applied Catalysis B: Environmental, 2020, vol. 268, 118474, total 31 pages.

\* cited by examiner

```
┌─────────────────────────────────────┐
│  The catalyst is disposed in a      │
│  continuous reactor                 │──202
└─────────────────────────────────────┘
                  ↓
┌─────────────────────────────────────┐
│  A gas is introduced into the       │
│  continuous reactor to undergo a    │
│  hydrogenation to form methane,     │──204
│  wherein the gas includes hydrogen  │
│  gas and carbon-oxygen-containing   │
│  compound                           │
└─────────────────────────────────────┘
```

FIG. 3

CATALYST FOR METHANATION REACTION AND METHOD FOR PREPARING METHANE

CROSS REFERENCE TO RELATED APPLICATIONS

This application claims the benefit of U.S. Provisional Application No. 63/277,836, filed on Nov. 10, 2021 and Application claims priority of Taiwan Patent Application No. 111126958, filed on Jul. 19, 2022, which is hereby incorporated herein by reference.

TECHNICAL FIELD

The disclosure relates to a catalyst for methanation reaction and a method for preparing methane.

BACKGROUND

Due to global warming and extreme climate caused by greenhouse gas emissions, advanced countries have begun to actively promote carbon-neutralized policies. In this context, industries that rely on fossil fuels (such as steel, petrochemical, and high-tech manufacturing industries) will face strong demand for carbon reduction. Therefore, it is necessary to actively introduce innovative technologies to achieve the goal of significantly reducing carbon emission.

Among them, the technology of using carbon dioxide from industrial flue gas as raw material and using catalysts to convert it into valuable chemicals has considerable potential. As the proportion of natural gas for power generation increases year by year, the application of converting carbon dioxide into methane (the main ingredient of natural gas) can not only provide raw materials for power generation, but also reduce carbon emissions. The technology, which employs carbon dioxide from industrial flue gas as raw material and specific catalyst to convert carbon dioxide into valuable chemicals, has considerable potential. As the proportion of power generation from natural gas for increases year by year, the application of converting carbon dioxide into methane (the main ingredient of natural gas) can not only provide raw materials for power generation, but also reduce carbon emissions.

Carbon dioxide can undergo a Sabatier reaction with hydrogen in the presence of a catalyst to produce methane and water. However, due to the strong exothermic characteristics of the Sabatier reaction, the specific surface area of the catalyst may be reduced by the heat generated during the reaction via thermal sintering, resulting in the deactivation of the catalyst.

Therefore, the industry needs a novel catalyst to overcome the problems mentioned above.

SUMMARY

The disclosure provides a catalyst for methanation reaction. According to embodiments of the disclosure, the catalyst includes a core, a shell, and an active metal. According to embodiments of the disclosure, the core can include cerium dioxide ($CeO_2$). According to embodiments of the disclosure, the shell encapsulates the core, and the shell includes zirconium dioxide ($ZrO_2$). According to embodiments of the disclosure, the active metal is in particle form and is disposed on the outer surface of the shell.

According to another embodiment of the disclosure, The disclosure provides a method for preparing methane. The method for preparing methane includes disposing the catalyst as claimed in claim 1 in a continuous reactor, and introducing a gas into the continuous reactor so that the gas undergoes a hydrogenation in the presence of the catalyst to form methane, wherein the gas includes hydrogen gas and carbon-oxygen-containing compound. According to embodiments of the disclosure, the gas includes hydrogen gas and carbon-oxygen-containing compound.

A detailed description is given in the following embodiments.

DETAILED DESCRIPTION

The catalyst for methanation reaction and method for preparing methane are described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. As used herein, the term "about" in quantitative terms refers to plus or minus an amount that is general and reasonable to persons skilled in the art.

The embodiments of the disclosure provide a catalyst for methanation reaction. According to embodiments of the disclosure, by means of the catalyst for methanation reaction of the disclosure, the carbon-oxygen-containing compound may react with hydrogen gas to undergo a methanation reaction (i.e. Sabatier reaction), thereby converting the carbon-oxygen-containing compound into methane. The catalyst for methanation reaction of the disclosure can have a core-shell structure. According to embodiments of the disclosure, the catalyst for methanation reaction of the disclosure includes a core, shell, and active metal, wherein the active metal is disposed on the shell. Since the catalyst for methanation reaction of the disclosure has a specific structure, ingredients and proportion of the ingredients, the thermal stability of the catalyst can be enhanced to prevent the core of catalyst from thermal sintering, thereby increasing the activity of the catalyst and improve the lifespan of the catalyst. As a result, when disposing the catalyst of the disclosure in the reactor (such as fixed bed reactor, fluidized bed reactor, or continuous agitated reactor) to perform the preparation of methane, the conversion of the carbon-oxygen-containing compound and the yield of methane may be effectively increased. In addition, the catalyst of the disclosure can be prepared from a large amount of cheap industrial by-products, resulting in reducing the carbon emission and the cost of process for preparing methane.

Figure 1:
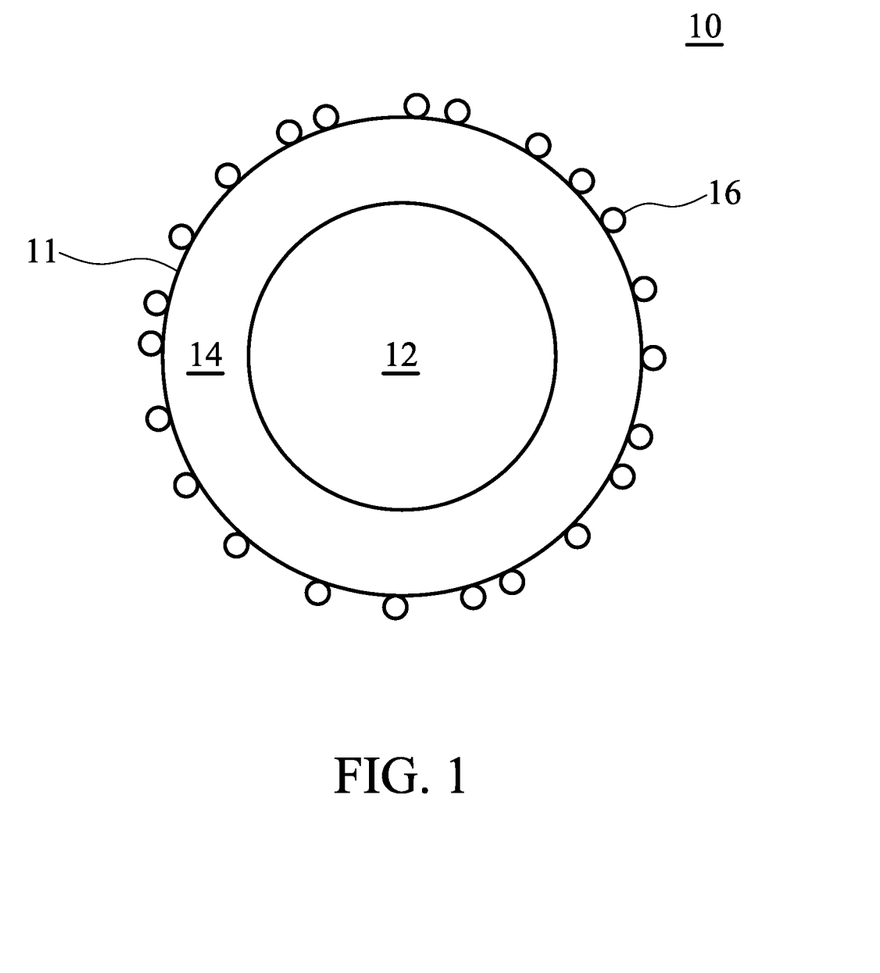
FIG. 1 is a cross-sectional view of the catalyst for methanation reaction according to an embodiment of the disclosure.

FIG. 1 is a cross-sectional view of the catalyst 10 for methanation reaction according to an embodiment of the disclosure. The catalyst 10 of the disclosure for methanation reaction can be a spherical-like particle and includes a core 12, a shell 14, and an active metal 16. According to embodiments of the disclosure, the shell 14 encapsulates the core 12, and the active metal 16 (in particular form) is disposed on an outer surface 11 of the shell 14.

According to embodiments of the disclosure, materials of the core of catalyst may act as an aid (for example, providing electron-hole pairs) to provide synergistic effects in methanation reactions, thereby facilitating the oxidation-reduction of carbon-oxygen-containing compound and hydrogen gas. In some embodiments of the disclosure, the carbon-oxygen-containing compound may be carbon monoxide (CO) or carbon dioxide ($CO_2$). According to embodiments of the disclosure, suitable materials of the core of the catalyst of the disclosure may include cerium dioxide ($CeO_2$). According to embodiments of the disclosure, the core of the catalyst for methanation reaction of the disclosure can consist of cerium dioxide (i.e. the core is cerium dioxide). According to some embodiments of the disclosure, the core can consist of a main ingredient and a minor ingredient, wherein the main ingredient may be cerium dioxide ($CeO_2$), and the minor ingredient may be lanthanum oxide ($La_2O_3$), yttrium oxide ($Y_2O_3$), samarium oxide ($Sm_2O_3$), or a combination thereof. According to embodiments of the disclosure, the amount of the main ingredient may be from 90 wt % to 99.9 wt % (such as 91 wt %, 92 wt %, 93 wt %, 94 wt %, 95 wt %, 96 wt %, 97 wt %, 98 wt %, or 99 wt %), and the amount of the minor ingredient may be from 0.1 wt % to 10 wt % (such as 0.2 wt %, 0.5 wt %, 1 wt %, 2 wt %, 3 wt %, 4 wt %, 5 wt %, 6 wt %, 7 wt %, 8 wt %, or 9 wt %), based on the total weight of the core. When the amount of the main ingredient is too low, the activity of the catalyst for methanation reaction of the disclosure would be greatly reduced. According to embodiments of the disclosure, the size of the core of the catalyst (i.e. the maximum distance between any two points on the core surface) may be about 10 nm to 200 nm, such as about 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, or 190 nm. The size of the core can be determined by transmission electron microscope (TEM).

According to some embodiments of the disclosure, the shell of the catalyst can serve as carrier for carrying the active metal and producing oxygen vacancy in the methanation reaction. In addition, since the shell encapsulates the core, the shell can slow down or prevent the core material (such as cerium dioxide) from thermal sintering due to the heat generated during the reaction process (i.e. avoiding excessive reduction of the specific surface area of the catalyst in the process of methanation reaction), thereby enhancing the thermal stability of the catalyst.

As a result, due to the high thermal stability of the catalyst of the disclosure, the activity of the catalyst in the methanation reaction would not be great reduced with prolonged reaction time.

According to embodiments of the disclosure, suitable materials of the shell of the catalyst of the disclosure may include zirconium dioxide ($ZrO_2$). According to embodiments of the disclosure, the shell of the catalyst for methanation reaction of the disclosure can consist of zirconium dioxide (i.e. the shell is zirconium dioxide). According to some embodiments of the disclosure, the shell can consist of a main ingredient and a minor ingredient, wherein the main ingredient may be zirconium dioxide ($ZrO_2$), and the minor ingredient may be titanium oxide ($TiO_2$), lanthanum oxide ($La_2O_3$), or a combination thereof. According to embodiments of the disclosure, the amount of the main ingredient may be 90 wt % to 99.9 wt % (such as 91 wt %, 92 wt %, 93 wt %, 94 wt %, 95 wt %, 96 wt %, 97 wt %, 98 wt %, or 99 wt %), and the amount of the minor ingredient may be 0.1 wt % to 10 wt % (such as 0.2 wt %, 0.5 wt %, 1 wt %, 2 wt %, 3 wt %, 4 wt %, 5 wt %, 6 wt %, 7 wt %, 8 wt %, or 9 wt %), based on the total weight of the shell. When the amount of the main ingredient is too low, the thermal stability and activity of the catalyst for methanation reaction of the disclosure would be great reduced.

According to embodiments of the disclosure, the thickness of the shell (i.e. the average distance between the inner surface (which contacts the core) and the outer surface) may be about 10 nm to 200 nm, such as about 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, or 190 nm. The thickness of the shell can be determined by transmission electron microscope (TEM).

According to embodiments of the disclosure, the weight ratio of the core to the shell may be about 2:1 to 8:1, such as about 3:1, 4:1, 5:1, 6:1, or 7:1. When the weight ratio of the core to the shell is too high, the catalyst exhibits poor thermal stability, thereby reducing the activity of the catalyst in the methanation reaction due to thermal sintering. When the weight ratio of the core to the shell is too low, the catalyst exhibits poor reactivity, thereby reducing the conversion of carbon dioxide and the yield of methane.

According to embodiments of the disclosure, the active metal disposed on the shell can facilitate the dissociation of the hydrogen gas in the methanation reaction. According to embodiments of the disclosure, the active metal may be nickel, rhodium, ruthenium, iridium, platinum, molybdenum, palladium, gold, silver, cobalt, manganese, copper, or a combination thereof. According to embodiments of the disclosure, the active metal is nickel. According to embodiments of the disclosure, the particle size of the active metal may be about 0.1 nm to 30 nm, such as about 0.2 nm, 0.5 nm, 1 nm, 2 nm, 3 nm, 4 nm, 5 nm, 6 nm, 7 nm, 8 nm, 9 nm, 10 nm, 15 nm, 20 nm, or 25 nm. According to embodiments of the disclosure, the amount of the active metal may be about 5 wt % to 30 wt % (such as about 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, or 29 wt %), based on the total weight of the core, shell and active metal. When the amount of the active metal is higher than the aforementioned floor, the catalyst exhibits superior reactivity, thereby improving the conversion of carbon dioxide and the yield of methane. When the amount of the active metal is lower than the aforementioned ceiling, the aggregation of the active metal on the shell can be inhibited and the active metal exhibits superior dispersibility, thereby enhancing the yield of methane. According to embodiments of the disclosure, the particle size of the catalyst (such as the maximum distance between any two points on the surface of the catalyst) may be about 20 nm to 250 nm, such as about 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, or 240 nm. The particle size of the catalyst can be determined by scanning electronic microscope (SEM). According to embodiments of the disclosure, the ratio of the size of the core and the thickness of the shell may be about 1:5 to 10:1, such as about 1:4, 1:3, 1:2, 1:1, 2:1, 3:1, 4:1, 5:1, 6:1, 7:1, 8:1, or 9:1. When the ratio of the size of the core and the thickness of the shell is too low, the catalyst exhibits poor reactivity, thereby reducing the conversion of carbon dioxide and the yield of methane. When the ratio of the size of the core and the thickness of the shell is too high, the catalyst exhibits poor thermal stability, thereby reducing the activity of the catalyst in the methanation reaction due to thermal sintering.

According to embodiments of the disclosure, the BET specific surface area of the catalyst may be about 50 $m^2/g$ to 250 $m^2/g$. The specific surface area is determined by the specific surface area instrument (Micromeritics Instrument Corporation ASAP2400).

According to some embodiments of the disclosure, in the catalyst for methanation reaction of the disclosure, the core is cerium dioxide, the shell is zirconium dioxide, and active metal is nickel. Herein, the amount of nickel in the catalyst may be about 10 atom % to 55 atom % (such as 15 atom %, 20 atom %, 25 atom %, 30 atom %, 35 atom %, 40 atom %, 45 atom %, or 50 atom %), the amount of cerium in the catalyst may be 25 atom % to 75 atom % (such as about 30 atom %, 35 atom %, 40 atom %, 45 atom %, 50 atom %, 55 atom %, 60 atom %, 65 atom %, or 70 atom %), and the amount of zirconium in the catalyst may be 6 atom % to 36 atom % (such as about 10 atom %, 15 atom %, 20 atom %, 25 atom %, 30 atom %, or 35 atom %), wherein the total amount of nickel, cerium and zirconium is set as 100 atom %. In embodiments of the disclosure, when the amount of nickel, cerium and zirconium of the catalyst for methanation reaction is within the aforementioned range and the catalyst has the specific core-shell structure (i.e. the core is cerium dioxide and the shell is zirconium dioxide), the catalyst of the disclosure exhibits higher thermal stability and reactivity, and the conversion of the carbon-oxygen-containing compound (such as carbon dioxide) and the yield of methane of the method for preparing methane employing the catalyst of the disclosure can be obviously improved.

Figure 2:
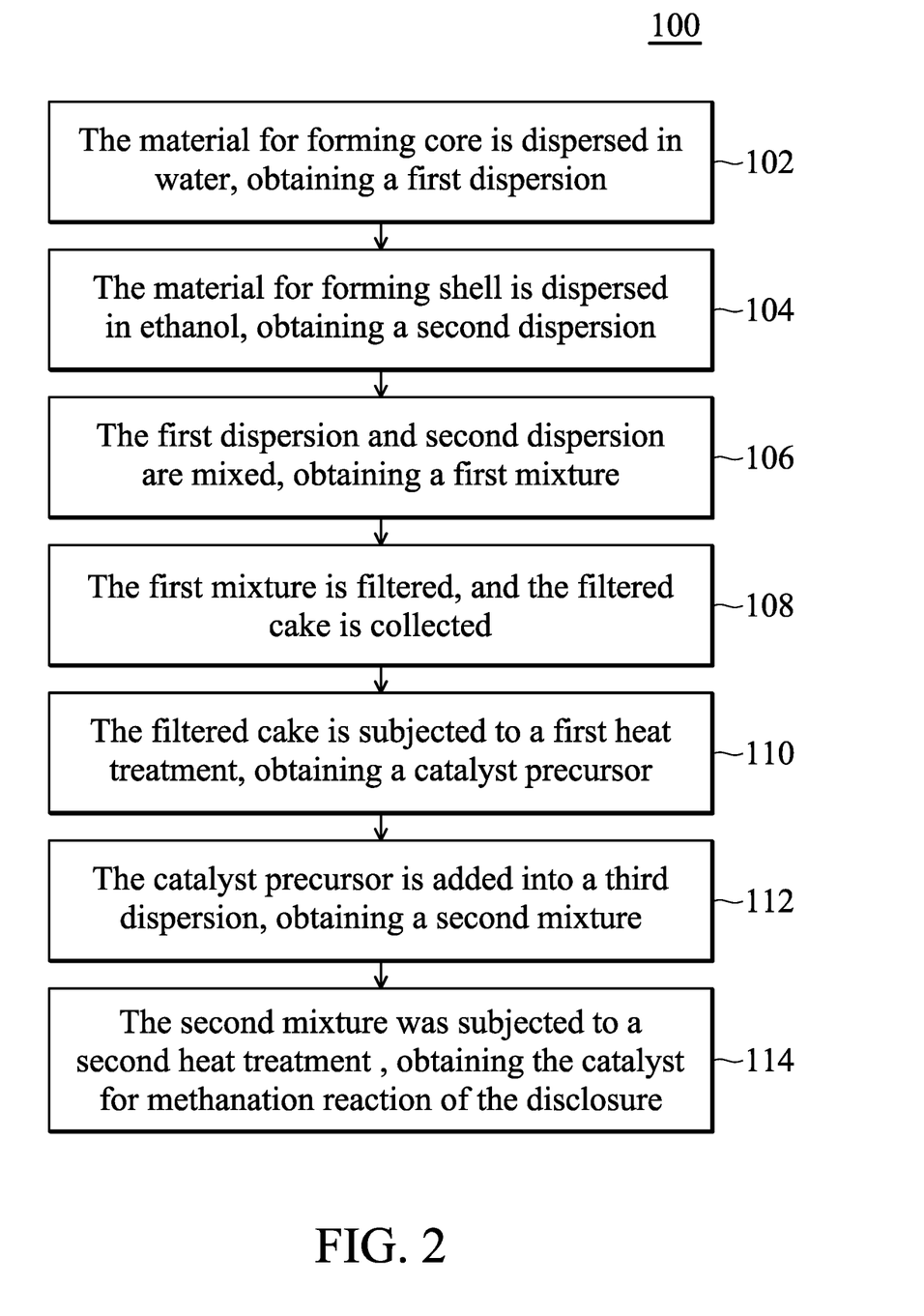
FIG. 2 is a flow chart illustrating the method 100 for preparing the catalyst for methanation reaction according to embodiments of the disclosure.

According to embodiments of the disclosure, as shown in FIG. 2, the method 100 for preparing the catalyst for methanation reaction of the disclosure 100 may include following steps. First, the material for forming core (such as cerium dioxide) is dispersed in water, obtaining a first dispersion (step 102). According to embodiments of the disclosure, the solid content of the first dispersion may be about 5 wt % to 50 wt %. Next, the material for forming shell (such as zirconium-containing precursor) is dispersed in ethanol, obtaining a second dispersion (step 104). According to embodiments of the disclosure, the solid content of the second dispersion may be about 5 wt % to 50 wt %. Next, the first dispersion and second dispersion are mixed, obtaining a first mixture (step 106). According to embodiments of the disclosure, in the first mixture, the weight ratio of the material for forming core (such as cerium dioxide) to the material for forming shell (such as zirconium-containing precursor) may be about 2:1 to 8:1. In the first mixture, the material for forming shell is disposed on the surface of the material for forming core via adsorption. In addition, according to some embodiments of the disclosure, the pH value of the first mixture can be further adjusted to a range from 8 to 13, in order to dispose the material for forming shell on the surface of the material for forming core via adsorption, and to avoid the particle size of the obtained catalyst being too large. Next, the first mixture is filtered, and the filter cake is collected (step 108). Next, the filter cake is subjected to a first heat treatment, obtaining a catalyst precursor (step 110). According to some embodiments of the disclosure, the temperature of the first heat treatment may be about 250° C. to 750° C., the time period of the first heat treatment may be 30 minutes to 24 hours, and the first heat treatment can be performed under oxidizing atmosphere, wherein the oxidizing atmosphere can be oxygen gas, or mixture of oxygen gas and inert gas. The inert gas may be argon gas, nitrogen gas, or a combination thereof. In the first heat treatment, the material for forming shell (such as a zirconium-containing precursor) forms a metal oxide (such as zirconium dioxide) via oxidation. According to embodiments of the disclosure, the catalyst precursor can have a core-shell structure, wherein the core-shell structure has a core and a shell, and the core is the material for forming core (such as cerium dioxide), and the shell is a metal oxide (such as zirconium dioxide). Next, the catalyst precursor is added into a third dispersion, obtaining a second mixture (step 112). The method for preparing the third dispersion includes dispersing an active metal precursor in water, wherein the solid content of the third dispersion may be about 20 wt % to 50 wt %. According to embodiments of the disclosure, in the second mixture, the weight ratio of the weight of active metal precursor to the total weight of the active metal precursor and catalyst precursor may be about 15:100 to 90:100. After removing the solvent of the second mixture, the result was subjected to a second heat treatment, obtaining the catalyst for methanation reaction of the disclosure (step 114). According to some embodiments of the disclosure, the temperature of the second heat treatment may be about 250° C. to 750° C., the time period of the second heat treatment may be 30 minutes to 12 hours, and the second heat treatment can be performed under reducing atmosphere, wherein the reducing atmosphere is hydrogen gas, or mixture of hydrogen gas and inert gas. The inert gas may be argon gas, nitrogen gas, or a combination thereof. According to embodiments of the disclosure, in the second heat treatment, the active metal precursor converts into active metal (such as nickel) via reduction.

According to embodiments of the disclosure, the material for forming shell may be zirconium-containing precursor, such as zirconium acetylacetonate, zirconium hexafluoro-acetylacetonate, zirconium naphthenate, zirconium methoxide, zirconium ethoxide, zirconium n-propoxide, zirconium isopropoxide, zirconium n-butoxide, zirconium isobutoxide, zirconium t-butoxide, or a combination thereof. According to embodiments of the disclosure, the active metal precursor may be metal nitrate, such as nitric acid nickel, nitric acid platinum, nitric acid palladium, nitric acid silver, nitric acid cobalt, nitric acid manganese, nitric acid copper, or a combination thereof.

According to some embodiments of the disclosure, the material for forming core is cerium dioxide, and the material for forming shell is zirconium-containing precursor. According to embodiments of the disclosure, the cerium dioxide has a particle size distribution D90 of about 10 nm to 200 nm (such as about 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, or 190 nm). Herein, the particle size distribution D90 means that 90 vol % of the powder has a diameter less than the value defined by D90. According to embodiments of the disclosure, the particle size distribution D90 is measured according to the standard ISO 13322-1:2004.

Figure 3:
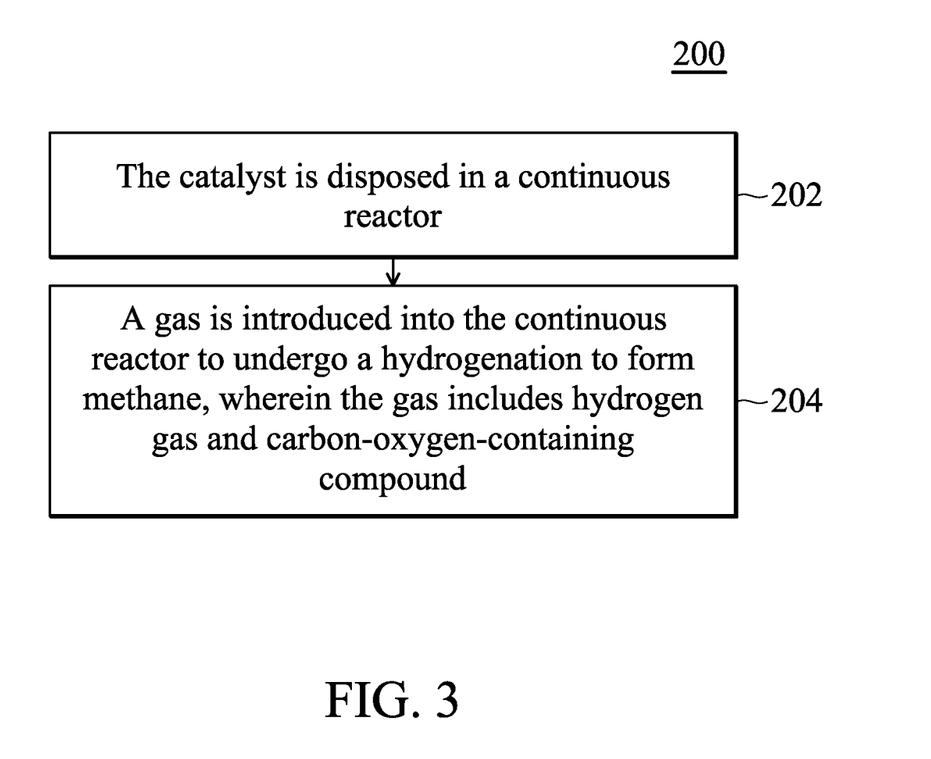
FIG. 3 is flow chart illustrating the method 200 for preparing methane according to embodiments of the disclosure.

According to embodiments of the disclosure, the disclosure also provides a method for preparing methane. As shown in FIG. 3, the method 200 for preparing methane may include following steps. First, the catalyst for methanation reaction of the disclosure is disposed in a continuous reactor (step 202). Next, a gas is introduced into the continuous reactor to undergo a hydrogenation to form methane, wherein the gas includes hydrogen gas and carbon-oxygen-containing compound (step 204). According to some embodiments of the disclosure, carbon-oxygen-containing compound converts to methane via hydrogenation. By means of introduction of hydrogen gas ($H_2$), the hydrogen gas reacts with carbon-oxygen-containing compound in the presence of the catalyst of the disclosure to form methane. The molar ratio of the hydrogen gas to the carbon-oxygen-containing compound can be adjusted according to the catalyst and reaction conditions. According to embodiments of the disclosure, the molar ratio of the hydrogen gas to the carbon-oxygen-containing compound may be about 3:1 to 10:1, such as about 4:1, 5:1, 6:1, 7:1, 8:1, or 9:1.

According to embodiments of the disclosure, the continuous reactor may be a fixed bed reactor, fluidized bed reactor, or continuous agitated reactor. According to embodiments of the disclosure, the carbon-oxygen-containing compound may be carbon monoxide, carbon dioxide, or a combination thereof. According to embodiments of the disclosure, the hydrogenation has a gas hourly space velocity (GHSV) about 500 $hr^{-1}$ to 50,000 $hr^{-1}$, such as about 1,000 $hr^{-1}$, 5,000 $hr^{-1}$, 10,000 $hr^{-1}$, 15,000 $hr^{-1}$, 20,000 $hr^{-1}$, 30,000 $hr^{-1}$, or 40,000 $hr^{-1}$. When the gas hourly space velocity of the hydrogenation is within the aforementioned range, the conversion of the carbon-oxygen-containing compound can be maintained during the preparation of methane in the presence of the catalyst of the disclosure.

According to embodiments of the disclosure, the temperature of the hydrogenation may be 180° C. to 400° C., such as about 200° C., 250° C., 300° C., or 350° C. When the temperature of the hydrogenation is too low, the conversion of the carbon-oxygen-containing compound is reduced. When the temperature of the hydrogenation is too high, the selectivity of methane is reduced. According to embodiments of the disclosure, the pressure of the hydrogenation may be about 1 $kg/cm^2$ to 20 $kg/cm^2$, such as about 2 $kg/cm^2$, 5 $kg/cm^2$, 10 $kg/cm^2$, or 15 $kg/cm^2$.

According to embodiments of the disclosure, the method for preparing methane can further include disposing a catalytic promoter in the continuous reactor so that the gas undergoes a hydrogenation in the presence of the catalyst and the catalytic promoter to form methane. According to embodiments of the disclosure, the catalytic promoter may be lanthanum-containing compound, yttrium-containing compound, gadolinium-containing compound, hafnium-containing compound, samarium-containing compound, neodymium-containing compound, or a combination thereof. According to embodiments of the disclosure, the amount of catalytic promoter may be 0.1 wt % to 10 wt %, based on the total weight of the catalytic promoter and catalyst.

Below, exemplary embodiments will be described in detail so as to be easily realized by a person having ordinary knowledge in the art. The inventive concept may be embodied in various forms without being limited to the exemplary embodiments set forth herein.

EXAMPLES

Preparation of Catalyst

Preparation Example 1

85 parts by weight of cerium dioxide powder (having a particle size distribution D90 of 100 nm, commercially available from ALDDRICH with a trade number of Lot #1356553) was added into 5000 parts by weight of ethanol, obtaining a first dispersion after sufficiently stirring. 10 parts by weight of zirconium isopropoxide was added into 1000 parts by weight of ethanol, obtaining a second dispersion after sufficiently stirring. Next, 500 parts by weight of first dispersion was mixed with 100 parts by weight of second dispersion, obtaining a first mixture after sufficiently stirring for 30 minutes. Next, the pH value of the first mixture was adjusted to 10 by $NH_4OH$ solution (1M, dissolved in ethanol). Next, the first mixture was heated to 30° C. and stood for 2 hours. After cooling the first mixture to room temperature, the result was filtered and filter cake was collected. Next, the filter cake was subjected to a first heat treatment under oxidizing atmosphere (including 20% of oxygen gas and 80% of argon gas), obtaining a catalyst precursor (i.e. a complex with a core-shell structure, wherein the core was cerium dioxide, and the shell was zirconium dioxide). The temperature of the first heat treatment was about 350° C., and the time period of the first heat treatment was about 2 hours. In the first heat treatment, isopropanol zirconium adsorbed on the surface of cerium dioxide converted into zirconium dioxide via oxidation. 47 parts by weight of nitric acid nickel was added into 2000 parts by weight of water, obtaining a third dispersion after sufficiently stirring. Next, 88 parts by weight of catalyst precursor was added into 2047 parts by weight of third dispersion, obtaining a second mixture after stirring for 30 minutes. Finally, the solvent of the second mixture was removed by rotary evaporator and dried at 110° C., and the result was subjected to a second heat treatment (calcination) under reducing atmosphere (including 10% hydrogen gas and 90% argon gas), obtaining Catalyst (1) (having a core-shell structure: cerium dioxide core, zirconium dioxide shell, and nickel metal disposed on the shell). the temperature of the second heat treatment was about 350° C., and the time period of the second heat treatment was about 2 hours. In the second heat treatment, nitric acid nickel converted to metal nickel via reduction. Catalyst (1) was analyzed by transmission electron microscope (TEM) and Catalyst (1) had a core-shell structure, wherein the size of the core (cerium dioxide) was about 30 nm to 50 nm, and the thickness of the shell (zirconium dioxide) was about 20 nm to 30 nm.

Comparative Preparation Example 1

85 parts by weight of cerium dioxide powder (having a particle size distribution D90 of 100 nm, commercially available from ALDDRICH with a trade number of Lot #1356553) and 10 parts by weight of zirconium dioxide powder (commercially available from Saint-Gobain NorPro with a trade number of SZ31163) was added into 5000 parts by weight of water, obtaining a first dispersion after sufficiently stirring. 47 parts by weight of nitric acid nickel was added into 2000 parts by weight of water, obtaining a second dispersion after sufficiently stirring. Next, the first dispersion was added into the second dispersion, obtaining a first mixture after stirring for 30 minutes. After removing the solvent of the second mixture by rotary evaporator and drying the result at 110° C., the result was subjected to a second heat treatment (calcination) under reducing atmosphere (including 10% hydrogen gas and 90% argon gas), obtaining Catalyst (2). In Catalyst (2), the metal nickel was disposed on the surface of cerium dioxide and zirconium dioxide powder, but Catalyst (2) did not have core-shell structure. In Catalyst (2), cerium dioxide and zirconium dioxide were randomly mixed and sintered.

Comparative Preparation Example 2

85 parts by weight of zirconium dioxide powder (commercially available from Saint-Gobain NorPro with a trade number of SZ31163) was added into 5000 parts by weight of water, obtaining a first dispersion after sufficiently stirring. 47 parts by weight of nitric acid nickel was added into 2000 parts by weight of water, obtaining a second dispersion after sufficiently stirring. Next, the first dispersion was added into the second dispersion, obtaining a mixture after stirring for 30 minutes. After removing the solvent of the second mixture by rotary evaporator and drying the result at 110° C., the result was subjected to a second heat treatment (calcination) under reducing atmosphere (including 10% hydrogen gas and 90% argon gas), obtaining Catalyst (3) (i.e. zirconium dioxide having metal nickel disposed on the surface thereof).

Comparative Preparation Example 3

85 parts by weight of cerium dioxide powder (having a particle size distribution D90 of 100 nm, available from ALDDRICH with a trade number of Lot #1356553) was added into 5000 parts by weight of water, obtaining a first dispersion after sufficiently stirring. 47 parts by weight of nitric acid nickel was added into 2000 parts by weight of water, obtaining a second dispersion after sufficiently stirring. Next, the first dispersion was added into the second dispersion, obtaining a mixture after stirring for 30 minutes. After removing the solvent of the second mixture by rotary evaporator and drying the result at 110° C., the result was subjected to a second heat treatment (calcination) under reducing atmosphere (including 10% hydrogen gas and 90% argon gas), obtaining catalyst (4) (i.e. cerium dioxide having metal nickel disposed on the surface thereof).

Preparation of Methane from Carbon Dioxide Via Catalyst

Example 1

The catalysts of Preparation Example and Comparative Preparation Example were disposed on the fixed bed reactor individually. Next, the mixture of hydrogen gas ($H_2$) and carbon dioxide ($CO_2$) (the molar ratio of hydrogen gas to carbon dioxide was 3:1) was introduced into the fixed bed reactor to undergo hydrogenation at a gas hourly space velocity of 500 $hr^{-1}$, gauge pressure of 1 $kg/cm^2$ and various temperature (as shown in Table 1). The result was analyzed by on-line gas chromatography (on-line GC) to determine the yield of methane. For convenience of comparison, as shown in Table 1, the measured yields of methane were represented relative to each other, wherein the yield of methane in the process employing Catalyst (1) was considered as 100%.

TABLE 1

| Gas hourly space velocity | | Temperature | | |
|---|---|---|---|---|
| (GHSV) of 500 $hr^{-1}$ | | 220(° C.) | 230(° C.) | 250(° C.) |
| Relative yield of methane(%) | Catalyst (1) (cerium dioxide core, zirconium dioxide shell, and nickel metal disposed on the shell) | 100 | 100 | 100 |
| | Catalyst (2) (randomly mixed and sintered cerium dioxide and zirconium dioxide with metal nickel ) | 90.71 | 94.65 | 97.24 |
| | Catalyst (3) (zirconium dioxide with metal nickel disposed on surface) | 61.31 | 85.97 | 96.01 |
| | Catalyst (4) (cerium dioxide with metal nickel disposed on surface) | 2.02 | 18.74 | 35.48 |

Example 2

The catalysts of Preparation Example and Comparative Preparation Example were disposed on the fixed bed reactor individually. Next, the mixture of hydrogen gas ($H_2$) and carbon dioxide ($CO_2$) (the molar ratio of hydrogen gas to carbon dioxide was 3:1) was introduced into the fixed bed reactor to undergo hydrogenation at a gas hourly space velocity of 1,000 $hr^{-1}$, gauge pressure of 1 $kg/cm^2$ and various temperature (as shown in Table 2). The result was analyzed by on-line gas chromatography (on-line GC) to determine the yield of methane. For convenience of comparison, as shown in Table 2, the measured yields of methane were represented relative to each other, wherein the yield of methane in the process employing Catalyst (1) was considered as 10000.

TABLE 2

| Gas hourly space velocity | | Temperature | | |
|---|---|---|---|---|
| (GHSV) of 1,000 $hr^{-1}$ | | 220(° C.) | 230(° C.) | 250(° C.) |
| Relative yield of methane(%) | Catalyst (1) (cerium dioxide core, zirconium dioxide shell, and nickel metal disposed on the shell) | 100 | 100 | 100 |
| | Catalyst (2) (randomly mixed and sintered cerium dioxide and zirconium dioxide with metal nickel ) | 31.45 | 46.06 | 76.21 |
| | Catalyst (3) (zirconium dioxide with metal nickel disposed on surface) | 19.80 | 42.00 | 58.70 |
| | Catalyst (4) (cerium dioxide with metal nickel disposed on surface) | 0.90 | 9.50 | 19.90 |

Example 3

The catalysts of Preparation Example and Comparative Preparation Example were disposed on the fixed bed reactor individually. Next, the mixture of hydrogen gas ($H_2$) and carbon dioxide ($CO_2$) (the molar ratio of hydrogen gas to carbon dioxide was 3:1) was introduced into the fixed bed reactor to undergo hydrogenation at a gas hourly space velocity of 2,500 $hr^{-1}$, gauge pressure of 1 $kg/cm^2$ and various temperature (as shown in Table 3). The result was analyzed by on-line gas chromatography (on-line GC) to determine the yield of methane. For convenience of comparison, as shown in Table 3, the measured yields of methane were represented relative to each other, wherein the yield of methane in the process employing Catalyst (1) was considered as 100%.

TABLE 3

| Gas hourly space velocity (GHSV) of 2,500 $hr^{-1}$ | | Temperature | | |
|---|---|---|---|---|
| | | 220(° C.) | 230(° C.) | 250(° C.) |
| Relative yield of methane(%) | Catalyst (1) (cerium dioxide core, zirconium dioxide shell, and nickel metal disposed on the shell) | 100 | 100 | 100 |
| | Catalyst (2) (randomly mixed and sintered cerium dioxide and zirconium dioxide with metal nickel) | 92.11 | 94.66 | 91.26 |
| | Catalyst (3) (zirconium dioxide with metal nickel disposed on surface) | 57.89 | 86.24 | 70.30 |
| | Catalyst (4) (cerium dioxide with metal nickel disposed on surface) | 2.63 | 19.51 | 23.83 |

Example 4

The catalysts of Preparation Example and Comparative Preparation Example were disposed on the fixed bed reactor individually. Next, the mixture of hydrogen gas ($H_2$) and carbon dioxide ($CO_2$) (the molar ratio of hydrogen gas to carbon dioxide was 3:1) was introduced into the fixed bed reactor to undergo hydrogenation at a temperature of 250° C., gauge pressure of 1 $kg/cm^2$ and various gas hourly space velocity (as shown in Table 4). The result was analyzed by on-line gas chromatography (on-line GC) to determine the yield of methane. For convenience of comparison, as shown in Table 4, the measured yields of methane were represented relative to each other, wherein the yield of methane in the process employing Catalyst (1) was considered as 10000.

TABLE 4

| Temperature (250° C.) | | Gas hourly space velocity (GHSV) | |
|---|---|---|---|
| | | 5,000($hr^{-1}$) | 10,000 ($hr^{-1}$) |
| Relative yield of methane(%) | Catalyst (1) (cerium dioxide core, zirconium dioxide shell, and nickel metal disposed on the shell) | 100 | 100 |
| | Catalyst (2) (randomly mixed and sintered cerium dioxide and zirconium dioxide with metal nickel) | 87.31 | 62.03 |
| | Catalyst (3) (zirconium dioxide with metal nickel disposed on surface) | 54.53 | 44.78 |
| | Catalyst (4) (cerium dioxide with metal nickel disposed on surface) | 22.21 | 18.67 |

As shown in Tables 1-4, in comparison with the catalyst prepared by physical mixing (i.e. Catalyst (2) of Comparative Preparation Example 1 (without core-shell structure)), the methanation process employing the catalyst of the disclosure (i.e. Catalyst (1) of Preparation Example 1) exhibits superior yield of methane under various gas hourly space velocity (GHSV) and various temperature.

In addition, as shown in Tables 1-4, in comparison with Catalyst (3) of Comparative Preparation Example 2 (which is zirconium dioxide with metal nickel disposed on surface) and Catalyst (4) of Comparative Preparation Example 3 (which is cerium dioxide with metal nickel disposed on surface), the methanation process employing the catalyst of the disclosure (i.e. Catalyst (1) of Preparation Example 1) exhibits superior yield of methane under various gas hourly space velocity (GHSV) and various temperature.

Table 5 shows particle sizes of cerium dioxide powder and cerium dioxide encapsulated by zirconium-containing precursor before and after calcination (700° C.) and the particle size was determined by measuring full width at half maximum at various 2θ signal of X-ray diffraction (XRD).

TABLE 5

| | particle size (Å) of cerium dioxide | |
|---|---|---|
| | before calcination | after calcination |
| cerium dioxide powder | 221.0 | 266.8 |
| cerium dioxide encapsulated by zirconium-containing precursor | 203.8 | 215.0 |

As shown in Table 5, the particle size of cerium dioxide powder (without any material disposed on the surface of the cerium dioxide) after calcination is about 1.2 times greater than that of cerium dioxide powder before calcination. In addition, the particle size of cerium dioxide encapsulated by zirconium-containing precursor after calcination (i.e. forming a zirconium dioxide/cerium dioxide particle with core-shell structure (cerium dioxide core and zirconium dioxide shell) is about 1.05 times greater than that of cerium dioxide encapsulated by zirconium-containing precursor before calcination.

The catalyst for methanation reaction of the disclosure is prepared by encapsulating zirconium-containing precursor on the cerium dioxide and then subjecting the result to calcination. Therefore, a large increase in the particle size of cerium dioxide as the core can be suppressed (as shown in Table 5). As a result, it is easier to provide electron/hole pairs through the quantum tunneling effect due to the smaller particle size of cerium dioxide core, thereby facilitating the oxidation-reduction reaction between carbon oxides and hydrogen.

Accordingly, since the catalyst for methanation reaction of the disclosure has a specific structure, ingredients and proportion of the ingredients, the thermal stability of the catalyst can be enhanced to prevent the core of catalyst from thermal sintering, thereby increasing the activity of the catalyst and improve the lifespan of the catalyst. As a result, when disposing the catalyst of the disclosure in the reactor to perform the preparation of methane, the conversion of the carbon-oxygen-containing compound and the yield of methane may be effectively increased.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A catalyst for methanation reaction, comprising:
a core, wherein the core comprises cerium dioxide ($CeO_2$);
a shell encapsulating the core, wherein the shell comprises zirconium dioxide ($ZrO_2$); and
an active metal, wherein the active metal is in particle form and is disposed on an outer surface of the shell.

2. The catalyst for methanation reaction as claimed in claim 1, wherein a weight ratio of the core to the shell is 2:1 to 8:1.

3. The catalyst for methanation reaction as claimed in claim 1, wherein the core consists of cerium dioxide.

4. The catalyst for methanation reaction as claimed in claim 1, wherein the shell consists of zirconium dioxide.

5. The catalyst for methanation reaction as claimed in claim 1, wherein the active metal is nickel, rhodium, ruthenium, iridium, platinum, molybdenum, palladium, gold, silver, cobalt, manganese, copper, or a combination thereof.

6. The catalyst for methanation reaction as claimed in claim 1, wherein an amount of the active metal is 5 wt % to 30 wt %, based on the total weight of the core, shell and active metal.

7. The catalyst for methanation reaction as claimed in claim 1, wherein the catalyst is spherical-like particle.

8. The catalyst for methanation reaction as claimed in claim 1, wherein a particle size of the catalyst is 20 nm to 250 nm.

9. The catalyst for methanation reaction as claimed in claim 1, wherein a particle size of the active metal is 0.1 nm to 30 nm.

10. The catalyst for methanation reaction as claimed in claim 1, wherein the active metal is nickel, wherein an amount of nickel in the catalyst is 10 atom % to 55 atom %, an amount of cerium in the catalyst is 25 atom % to 75 atom %, and an amount of zirconium is 6 atom % to 36 atom %, wherein a total amount of nickel, cerium and zirconium is 100 atom %.

11. A method for preparing methane, comprising:
disposing the catalyst as claimed in claim 1 in a continuous reactor; and
introducing a gas into the continuous reactor so that the gas undergoes a hydrogenation in a presence of the catalyst to form methane, wherein the gas comprises hydrogen gas and carbon-oxygen-containing compound.

12. The method for preparing methane as claimed in claim 11, further comprising:
disposing a catalytic promoter in the continuous reactor so that the gas undergoes a hydrogenation in a presence of the catalyst and the catalytic promoter to form methane.

13. The method for preparing methane as claimed in claim 12, wherein the catalytic promoter is lanthanum-containing compound, yttrium-containing compound, gadolinium-containing compound, hafnium-containing compound, samarium-containing compound, neodymium-containing compound, or a combination thereof.

14. The method for preparing methane as claimed in claim 12, wherein an amount of the catalytic promoter is 0.1 wt % to 10 wt %, based on the total weight of the catalytic promoter and the catalyst.

15. The method for preparing methane as claimed in claim 11, wherein the continuous reactor is a fixed bed reactor, fluidized bed reactor, or continuous agitated reactor.

16. The method for preparing methane as claimed in claim 11, wherein the carbon-oxygen-containing compound is carbon monoxide, carbon dioxide, or a combination thereof.

17. The method for preparing methane as claimed in claim 11, wherein a molar ratio of the hydrogen gas to the carbon-oxygen-containing compound is 3:1 to 10:1.

18. The method for preparing methane as claimed in claim 11, wherein the hydrogenation has a gas hourly space velocity (GHSV) of 500 $hr^{-1}$ to 50000 $hr^{-1}$.

19. The method for preparing methane as claimed in claim 11, wherein the hydrogenation has a reaction temperature of 180° C. to 400° C.

20. The method for preparing methane as claimed in claim 11, wherein the hydrogenation has a reaction pressure of 1 $kg/cm^2$ to 20 $kg/cm^2$.

* * * * *